United States Patent

Sun

(10) Patent No.: US 6,312,805 B1
(45) Date of Patent: Nov. 6, 2001

(54) CATIONIC DYEABILITY MODIFIER FOR USE WITH POLYESTER AND POLYAMIDE

(75) Inventor: Yanhui Sun, Wilmington, DE (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/502,322

(22) Filed: Feb. 11, 2000

(51) Int. Cl.$^7$ .................. D02G 3/00; C08F 20/00
(52) U.S. Cl. .................. 428/364; 528/272; 528/288; 528/293; 528/302; 525/437; 525/444; 525/540; 560/1; 560/147; 562/400; 562/512; 562/552
(58) Field of Search ............... 528/272, 288, 528/293, 302; 525/437, 444, 540; 560/1, 147; 562/400, 512, 552; 428/364

(56) References Cited

U.S. PATENT DOCUMENTS

| | | |
|---|---|---|
| 3,018,272 | 1/1962 | Griffing et al. . |
| 3,167,531 | 1/1965 | Parker et al. . |
| 3,296,204 | 1/1967 | Caldwell . |
| 3,313,778 | 4/1967 | Sakurai et al. . |
| 3,454,535 | 7/1969 | Bodesheim et al. . |
| 3,636,131 | 1/1972 | Davis et al. ............ 260/75 S |
| 3,671,379 | 3/1971 | Evans et al. ............ 161/173 |
| 3,706,712 | 12/1972 | Davis et al. ............ 260/75 S |
| 4,042,618 | 8/1977 | Davis et al. ............ 260/470 |
| 4,259,682 | 3/1981 | Gamo ............ 357/55 |
| 4,415,726 | 11/1983 | Tanji et al. ............ 528/272 |
| 4,426,516 | 1/1984 | Kuriki et al. ............ 528/272 |
| 4,496,505 | 1/1985 | Tanji et al. ............ 264/101 |
| 4,508,674 | 4/1985 | Kuriki et al. ............ 264/234 |
| 4,539,805 | 9/1985 | Ukai et al. ............ 57/290 |
| 4,668,764 | 5/1987 | Satou ............ 528/308.1 |
| 4,986,483 | 1/1991 | Ryu et al. ............ 242/45 |
| 5,108,675 | 4/1992 | Matsuo et al. ............ 264/103 |
| 5,370,929 | 12/1994 | Handa et al. ............ 428/364 |
| 5,559,205 | 9/1996 | Hansen et al. ............ 538/279 |
| 5,662,716 | 9/1997 | Sun . | 
| 5,782,935 | 7/1998 | Hirt et al. ............ 8/512 |

FOREIGN PATENT DOCUMENTS

| | | |
|---|---|---|
| 0 843 030 A1 | 5/1998 | (EP) . |
| 1 006 220 A1 | 6/2000 | (EP) . |
| 1 016 741 A1 | 7/2000 | (EP) . |
| 1 033 422 A1 | 9/2000 | (EP) . |
| 5-30221 | 11/1993 | (JP) . |
| 7-53699 | 2/1995 | (JP) . |
| 8-269820 | 10/1996 | (JP) . |
| 11-200175 | 7/1999 | (JP) . |
| 11-302919 | 11/1999 | (JP) . |
| 97/05308 | 2/1997 | (WO) . |

OTHER PUBLICATIONS

Traub et al., Dyeing properties of poly(trimethylene terephthalate) fibres, *Melliand*, E175–E180, Sep. 1995.
Traub, H.L., Synthesis and Textile Chemical Properties of Polytrimethyleneterephthalate, *Dissertation*, Feb. 1994.
PCT International Search Report for PCT/US01/02655.
European Patent Office Abstracts of Japan 07053699.

Primary Examiner—Samuel A. Acquah

(57) ABSTRACT

A cationic dyeability modifier for incorporation into polyesters and polyamides to increase their affinity for basic dyes, said cationic dyeability modifier having the following formula:

$$R_1OOC-(CH_2)_n-CH(CH_2CH_2SO_3X)-(CH_2)_m-COOR_2$$

where n is an integer from 1 to 10, m is an integer from 1 to 10, X is an alkali metal selected from the group consisting of lithium, sodium and potassium, and $R_1$ and $R_2$ are independently selected from hydrogen and alkyl groups having one to four carbon atoms is disclosed. Basic dyeable copolyesters and copolyamides containing the cationic dyeability modifier incorporated into the polymer chain of the copolymer are also disclosed. A process for preparing a basic dyeable copolyester by combining poly(alkylene terephthalate)-forming monomers or polyoxyalkylene glycol oligomers with the cationic dyeability modifier, and mixing and heating at a temperature sufficient to cause copolymerization to form a copolyester is also disclosed.

24 Claims, No Drawings

CATIONIC DYEABILITY MODIFIER FOR USE WITH POLYESTER AND POLYAMIDE

FIELD OF THE INVENTION

This invention relates to a cationic dyeability modifier that provides improved basic dyeability for polyesters and polyamides. The invention also relates to a basic dyeable copolyester derived from polyesters such as poly(alkylene terephthalates) and to a basic dyeable copolyamide derived from polyamides such as nylon 6 and nylon 66. The modified polyester and modified polyamide are suitable for use in manufacturing fibers, filaments and other useful articles.

BACKGROUND OF THE INVENTION

Polyesters, especially polyalkylene terephthalates, and polyamides, especially nylon 6 and nylon 66, have excellent physical and chemical properties and have been widely used for resins, films and fibers. In particular, polyester and polyamide fibers have relatively high melting points, and can attain high orientation and crystallinity. Accordingly, polyesters and polyamides have excellent fiber properties such as chemical, heat and light stability, and high strength.

However, polyesters, especially polyester fibers, are difficult to dye. The molecular structure and the high levels of orientation and crystallinity that impart desirable properties to the polyester also contribute to a resistance to coloration by dye compounds. Also contributing to the difficulty in dyeing polyester is the characteristics that polyesters, unlike protein fibers, do not have dye sites within the polymer chain that are reactive to basic or acid dye compounds. Although polyamides are not as difficult to dye as polyesters, one or more dyeability additives are nevertheless commonly incorporated into polyamides, e.g., in order to selectively increase the affinity of the polyamide fibers for certain types of dyes, e.g., acidic or basic, or to selectively increase the resistance of the fibers to staining with certain types of staining agents.

It is known that that certain materials, such as aromatic sulfonates and their sodium salts, including the sodium salt of 5-sulfoisophthalic acid or the sodium salt of dimethyl 5-sulfoisophthalate, can be copolymerized with the polyester or polyamide as a means of conferring basic dyeability. Other cationic dyeability modifiers have also been disclosed. For example, Sakurai, U.S. Pat. No. 3,313,778, discloses a modified polyester which has linked to the main chain thereof a minor proportion of at least one organo sulfonic acid ester having the formula $(X—SO_2—O)_n—Y$, where n is an integer from 1 to 4; X is, e.g., an alkyl group of 1 to 12 carbon atoms; and Y is, e.g., a lower alkyl group, having one or two ester-forming functional groups, for example beta-carbomethoxyethyl methanesulfonate.

Further, poly(trimethylene terephthalate) has many properties that make it desirable for use in manufacturing fibers for textile applications, including improved recovery and resilience, as compared with poly(ethylene terephthalate). However, cationic dyeability modifiers that are particularly useful for improving the basic dyeability of poly(trimethylene terephthalate) have not been proposed.

It is desireable to provide a cationic dyeability modifier which can be incorporated into polyesters, especially poly(alkylene terephthalate), and polyamides, especially nylon 6 and nylon 66, to confer improved basic dyeability and which can be produced at lower cost than conventional cationic dyeability modifiers.

It is also desirable to provide a basic dyeable polyester, in particular poly(alkylene terephthalate), and more particularly poly(trimethylene terephthalate), which can be easily processed into fibers, films or other shaped articles and basic-dyed without the use of expensive cationic dyeability modifiers or additives, special solutions, and/or complicated application procedures.

It is also desireable to provide a basic dyeable polyamide, in particular nylon 6 or nylon 66, which can be easily processed into fibers, films or other shaped articles and basic-dyed without the use of expensive cationic dyeability modifiers or additives, special solutions, and/or complicated application procedures. The present invention provides such a cationic dyeability modifier and basic dyeable polyester and polyamide.

SUMMARY OF THE INVENTION

The invention comprises a cationic dyeability modifier for incorporation into polyesters and polyamides to increase their affinity for basic dyes, said cationic dyeability modifier having the following formula:

$$R_1OOC—(CH_2)_n—CH(CH_2CH_2SO_3X)—(CH_2)_m—COOR_2$$

where n is an integer from 1 to 10, m is an integer from 1 to 10, X is an alkali metal selected from the group consisting of lithium, sodium and potassium, and $R_1$ and $R_2$ are independently selected from hydrogen and alkyl groups having one to four carbon atoms.

The invention further comprises a basic dyeable copolymer selected from the group consisting of copolyesters and copolyamides, wherein said copolymer comprises a comonomer of the formula:

$$R_1OOC—(CH_2)_n—CH(CH_2CH_2SO_3X)—(CH_2)_m—COOR_2$$

where n is an integer from 1 to 10, m is an integer from 1 to 10, X is an alkali metal selected from the group consisting of lithium, sodium and potassium, and $R_1$ and $R_2$ are independently selected from hydrogen and alkyl groups having one to four carbon atoms, and wherein said comonomer is incorporated into the polymer chain of said copolymer in an amount sufficient to improve its affinity for basic dyes.

The invention further comprises a process for preparing a basic dyeable copolyester comprising the steps of: (a) combining one or more materials selected from the group consisting of poly(alkylene terephthalate)-forming monomers and polyoxyalkylene glycol oligomers with a comonomer of the formula:

$$R_1OOC—(CH_2)_n—CH(CH_2CH_2SO_3X)—(CH_2)_m—COOR_2$$

where n is an integer from 1 to 10, m is an integer from 1 to 10, X is an alkali metal selected from the group consisting of lithium, sodium and potassium, and $R_1$ and $R_2$ are independently selected from hydrogen and alkyl groups having one to four carbon atoms; and (b) mixing and heating said materials and said comonomer at a temperature sufficient to cause copolymerization to form a copolyester containing said comonomer in an amount sufficient to improve its affinity for basic dyes.

DETAILED DESCRIPTION OF THE INVENTION

The cationic dyeability modifier of the invention is an aliphatic sulfonate of the following formula:

$$R_1OOC—(CH_2)_n—CH(CH_2CH_2SO_3X)—(CH_2)_m—COOR_2 \qquad I$$

where n is an integer from 1 to 10, m is an integer from 1 to 10, X is an alkali metal selected from lithium, sodium and potassium, and $R_1$ and $R_2$ are independently selected from hydrogen and alkyl groups having one to four carbon atoms.

The preferred cationic dyeability modifier is 3-(2-sulfoethyl) hexanedioic acid, sodium salt, which has the following formula:

HOOC—(CH$_2$)—CH(CH$_2$CH$_2$SO$_3$Na)—(CH$_2$)$_2$—COOH  II and its dimethyl ester, namely dimethyl-3-(2-sulfoethyl) adipate, sodium salt, which has the following formula:

H$_3$COOC—(CH$_2$)—CH(CH$_2$CH$_2$SO$_3$Na)—(CH$_2$)$_2$—COOCH$_3$  III 3-(2-Sulfoethyl)hexanedioic acid, sodium salt is prepared by addition reaction of 4-vinyl cyclohexene and formic acid in the presence of hydrogen peroxide to form a mixture of 4-vinylcyclohexane 1,2-diformate, 4-vinylcyclohexane 1-monoformate, and 4-vinylcyclohexane 2-monoformate, followed by a hydrolysis with sodium hydroxide and then an addition reaction with sodium bisulfite and sodium persulfate in the presence of sodium hydroxide to form the sodium salt of 4-(2-sulfoethyl)cyclohexane-1,2-diol, followed by oxidation in the presence of tungstic acid and hydrogen peroxide to form 3-(2-sulfoethyl)hexanedioic acid, sodium salt, as set forth in greater detail in Examples I to III. Dimethyl-3-(2-sulfoethyl) adipate, sodium salt is prepared from 3-(2-sulfoethyl) hexanedioic acid, sodium salt by reaction with anhydrous methanol, as described in greater detail in Example IV.

The cationic dyeability modifier of formula I is incorporated into the polymer chain of a polyester or polyamide to provide dye sites for basic dyes. Polyester and polyamide copolymers containing the cationic dyeability modifiers of the invention, and fibers, films and other shaped articles made therefrom, have an improved affinity for basic dyes. Desirable results may be obtained using the aliphatic sulfonates of formula I with or without a dye opener ingredient polycondensed therewith.

The cationic dyeability modifier of formula I may be incorporated into the polyester or polyamide polymer chain by a variety of methods, including: (1) incorporating the cationic dyeability modifier into the polymer chain during polymerization; (2) adding the cationic dyeability modifier to the polymerized resin prior to melt-spinning or other forming operation; or (3) incorporating the cationic dyeability modifier into the polymer chain to form a highly sulfonated copolymer, which is then blended with unsulfonated polymer to form a basic dyeable copolyester. The preferred method is to incorporate the cationic dyeability modifier into the polymer during polyermization by adding the modifier to the other polymer-forming materials before any significant polymerization has taken place. For example, in the case of a dyeability modified poly(alkylene terephthalate), the cationic dyeability modifier is mixed with polyester-forming materials such as alkylene glycol, terephthalic acid, one or more lower dialkyl esters of terephthalic acid, and/or low molecular weight oligomers of alkylene glycol and terephthalic acid, and then copolymerized using standard polymerization procedures. For example, in the case of a dyeability modified polyamide, the cationic dyeability modifier is mixed with polyamide-forming materials, such as epsilon-caprolactam, adipic acid, and/or hexamethylene diamine at the salt stage, and then copolymerized using standard polymerization procedures. The cationic dyeability modifier of the invention can also be incorporated in a copolyester or copolyamide that is manufactured in a continuous process in a manner that is conventional for other copolymer-forming cationic dyeability modifiers.

In accordance with one embodiment of the invention, the cationic dyeability modifier is used to form a dyeability modified copolyester of poly(trimethylene terephthalate). In this embodiment, the cationic dyeability modifier is mixed with dimethylterephthalate and propylene glycol in a reactor. The temperature is raised to 180° C. to carry out the transesterification in the presence of titanium catalyst. As methanol by-product is evolved and removed, the temperature is slowly raised to 230° C. A vacuum is then applied to the system to gradually reduce the pressure to 0.5 mm Hg, and the temperature is raised to 250° C. The polymer viscosity is gradually increased. After about 1 hour under vacuum, the reaction is stopped and the polymer product is cooled down.

Generally, sufficient cationic dyeability modifier of formula I is used to produce a copolyester or copolyamide containing from 0.5 to 4 mole percent, preferably from 1 to 2 mole percent of the cationic dyeability modifier in the final copolymer. The cationic dyeability modifier may be incorporated into a polyester or polyamide in an amount up to 30 mole percent, preferably 20 to 25 mole percent, to form a highly sulfonated copolymer, which is then blended with unsulfonated polyester or polyamide to give a basic dyeable polyester having a mole percent sulfonate comonomer as set forth in the previous sentence.

The polyesters useful in the invention are poly(alkylene terephthalates), which are fiber-forming linear condensation polymers having ester linkages in the polymer chain. In the absence of an indication to the contrary, a reference to poly(alkylene terephthalates) is meant to encompass copolyesters, i.e., polyesters made using 2 or 3 or more monomeric reactants, each having two ester forming groups. The poly(alkylene terephthalates) may, if desired, contain various catalysts and/or additives, e.g., dye openers, delustrants, viscosity boosters, optical brighteners, toning pigments, color inhibitors and anti-oxidants. Examples of linear, fiber-forming polyesters useful in the present invention include poly(ethylene terephthalate), poly(trimethylene terephthalate), and poly(butylene terephthalate). Poly (trimethylene terephthalate) is preferred.

The polyamides useful in the invention include nylon 6, nylon 66 and various nylon copolymers.

As indicated above, the basic dyeable copolyesters and copolyamides according to the present invention have a relatively high affinity for basic dyes and can be dyed in a range of colors. More specifically, the copolyesters and copolyamides contain sulfonate groups which have a strong tendency to exchange the sodium cation with the dye cation of basic dyes. For example, the basic dyeable copolyesters and copolyamides may be spun into fibers and dyed in either continuous or staple form with basic dyes. By a "basic dye" is meant a colored cationic organic substance such as those containing sulfonium, oxonium or quaternary ammonium functional groups. The basic dye types include, for example, Victoria Green WB (C.I. Basic Green 4), a dye of the triphenyl methane type having the following chemical structure:

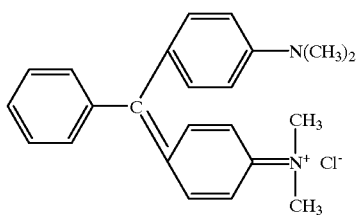

Victoria Pure Blue BO (C.I. Basic Blue 7), a triaryl methane type dye having the following chemical structure:

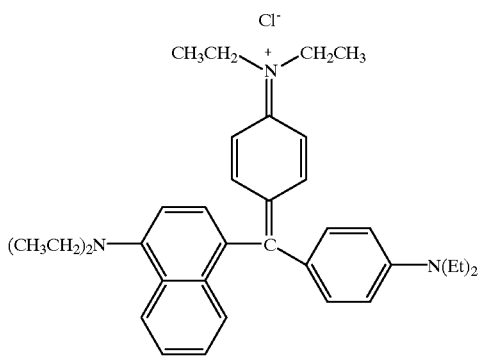

Sevron Blue 5G (C.I. Basic Blue 4), a dye of the oxazine type having the following chemical structure:

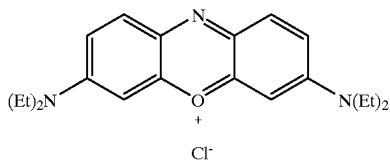

Brilliant Green B (C.I. Basic Green 1), a triphenyl methane type dye having the following chemical structure:

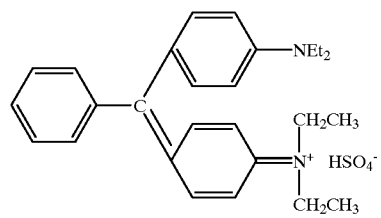

And Rhodamine B (C.I. Basic Violet 10), a dye of the xanthene type having the following chemical structure:

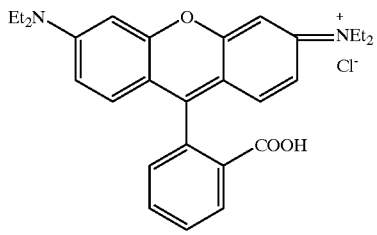

and the like. The dyes are preferably applied from an aqueous solution at a temperature of between 80° C. and 125° C.

The intrinsic viscosity measurements described herein were made by dissolving polymer samples in 50/50 weight percent trifluoroacetic acid/dichloromethane solvent mixture to yield a solution having a concentration of 0.4 g/dL. The viscosity of the resulting solution was measured using a Viscoteck Forced Flow Viscometer Model Y-900 at 19° C. and Viscoteck software version V5.7 to calculate the intrinsic viscosity (IV).

EXAMPLES

Example I

Preparation of mixture of 4-vinyl cyclohexane 1,2-diformate, 4-vinyl cyclohexane 1-monoformate and 4-vinyl cyclohexane 2-monoformate A one liter 3-necked round flask was equipped with a mechanical stirrer, one dropping funnel and a thermometer. 500 mL (10 mole) 96% formic acid and 130 mL (1 mole) 4-vinyl cyclohexene were charged to the flask. 106.9 g. (1.1 mole) 35% hydrogen peroxide solution was charged into the dropping funnel. The reaction flask was cooled in a water bath. Under stirring, hydrogen peroxide solution was dropped in at a rate of 1.5 mL per minute. After the addition was finished, the reaction mixture was stirred for two hours. The reaction temperature was kept below 30° C. When the reaction was complete, water and formic acid were distilled out under vacuum at 40–45° C. The residue oil was distilled under high vacuum in the presence of 2% cuprous chloride. The boiling point of the mixture of formates and a small amount of 4-vinylcyclohexane-1,2-diol was 100–118° C. at 0.1 mm Hg. The yield was 71–80%. The nuclear magnetic resonance ($^1$H NMR) spectra in $CDCl_3$ gave the following results: 1.5 (m, 1H), 1.58 (m, 1H), 1.72 (m, 1H), 1.81 (m, 1H), 2.4 (m, 1H), 3.0 (s, 1H), {3.35–3.82 (m, 1H), 4.74–4.91 (m, 1H) mixed isomer}, 4.98 (m, 2H), 5.72 (m, 1H), {7.99 (s, 1H), 8.03 (s, 1H) mixture of diformate and monoformate}. The residue oil can be used in the reaction described in Example II without the above-described purification.

Example II

Preparation of 4-(2-sulfoethyl)cyclohexane-1,2-diol, sodium salt

A one liter 4-necked round flask was equipped with mechanical stirrer, a dropping funnel and a thermometer. One mole of the mixture formed in the previous example was charged to the flask. Under stirring, 192 g. (1.2 mole) 25% sodium hydroxide solution was added dropwise at 20–25° C. The stirring was maintained for 30 minutes after the addition. Then the mixture was allowed to separate for about two hours. The bottom aqueous solution of sodium formate was discharged. To the flask, 180 g.of water was added. Then 109.3 g. sodium bisulfite (1.05 mol) in 180 g. water and 2.38 g. sodium persulfate (0.01 mol) in 20 g. water were added dropwise into the mixture simultanously from two dropping funnels under vigorous stirring at 20–25° C. The solution pH was maintained at about 6.3–6.6 by adding 12.5% sodium hydroxide solution occasionally. The solution was stirred for 2 hours after the addition. The conversion was almost 100%. The nuclear magnetic resonance ($^1$H NMR) spectra in $D_2O$ gave the following results: $^1$H NMR: 1.48–1.89 (m, 9H), 2.94 (m, 2H), {3.55–3.9 (m, 1H), 4.73–5.10 (m, 1H) mixed isomer}.

Example III

Preparation of 3-(2-sulfoethyl)hexanedioic acid, sodium salt

To the solution resulting from Example II, 291.6 g (3 mole) 35% hydrogen peroxide solution and 1.24 g. tungstic acid were charged. The mixture was heated slowly to reflux for 3 hours. (Caution must be taken during heating since some trace formic acid in the mixture can cause vigorous boiling.) The solution turned from yellow to clear and colorless. The pH of the solution was 2–3. The reaction mixture was concentrated to about 65% 3-(2-sulfoethyl)hexanedioic acid, sodium salt, and cooled down to room temperature to allow the sodium sulfate by-product to precipitate. After filtering the salt, the solution was stirred slowly to crystallize the 3-(2-sulfoethyl)hexanedioic acid, sodium salt product. White crystals of 3-(2-sulfoethyl)hexanedioic acid, sodium salt were filtered and recrystallized and dried. The nuclear magnetic resonance ($^1$H NMR) spectra showed the conversion of 4-(2-sulfoethyl)cyclohexane-formate, sodium salt to 3-(2-sulfoethyl)hexanedioic acid, sodium salt was 100%. The nuclear magnetic resonance ($^1$H NMR) spectra in ($CD_3OD$) gave the following results: 1.58 (m, 2H), 1.75 (m, 2H), 1.90 (m, 1H), 2.18 (d, 2H), 2.27 (t, 2H), 2.73 (t, 2H).

Example IV
Preparation of dimethyl-3-(2-sulfoethyl)adipate sodium salt 3-(2-Sulfoethyl) hexanedioic acid, sodium salt was converted to the dimethyl ester by reacting 35 equivalents of anhydrous methanol at reflux in the presence of 2 equivalents of toluene and 0.15 equivalent of sulfuric acid. After two hours reaction, the solvents were partially removed by distillation. The residue was neutralized to a pH of 6–7 and rotovapped to dryness. The crude product was extracted with a mixture of ethanol and methanol and dried to white solid. The nuclear magnetic resonance ($^1$H NMR) spectra in (CD$_3$OD) gave the following results: 1.57 (m, 2H), 1.72 (m, 2H), 1.90 (m, 1H), 2.23 (dd, 2H), 2.29 (t, 2H), 2.70 (t, 2H), 3.58 (s, 6H).

Comparative Example A
Comparative example: Polyester homopolymer containing no dyeability modifier A 5 liter three-necked flask was charged with 2,097.25 grams of dimethylterephthalate (10.8 mole), 1255.7 grams of 1,3-propanediol (16.5 moles), and 1.24 grams of a 10 weight percent solution of titanium tetraisobutoxide (Tyzor® TPT, DuPont Performance Chemicals) in isopropanol. The mixture was stirred and heated to 190° C. under nitrogen gas. Methanol was distilled within two hours. Then the flask was connected to a vacuum pump and the pressure lowered to 0.2 mm Hg. The mixture temperature was slowly raised to 250° C. and maintained at 250° C. for about two hours. The resulting final poly(trimethylene terephthalate) homopolymer had an intrinsic viscosity of 0.6 dl/g. The homopolymer was solid state polymerized at 200° C. under nitrogen purge for four hours, thereby increasing the intrinsic viscosity to 1.0 dl/g.

The homopolymer was ground into flakes, spun into fiber at 250° C. and dyed at 100° C. under atmospheric pressure in an aqueous bath containing one weight percent Sevron Blue (Crompton & Knowles, Gibralter, Pa.) based on fibers. The dyed fibers showed an off-white color.

Example V
Copolyester containing dyeability modifier of the invention

The procedure of Example IV was followed, except that 69 grams (0.22 mole) of dimethyl-3-(2-sulfoethyl)adipate, sodium salt were charged to the three-neck flask, along with the dimethylterephthalate and 1,3-propanediol. The final copolymer had an intrinsic viscosity of 0.6 dl/g, and was solid state polymerized to an intrinsic viscosity of 1.0 dl/g before spinning into fibers. The dyeability modified copolyester fibers turned a blue shade when dyed at 100° C. under atmospheric pressure with Sevron Blue.

Comparative Example B
Comparative example: Copolyester containing conventional dyeability modifier A 200 pound autoclave was charged with 69.9 pounds (31.7 kg) of dimethyl terephthalate (0.36 lb. mole, 163.3 mole), 41.93 pounds (19.0 kg) of 1,3-propanediol (0.55 lb. mole, 249.9 moles), 2.17 pounds (0.98 kg) of dimethyl sulfoisophthalate, sodium salt (0.007 lb. mole), and 9.97 grams of Tyzor TPT. The mixture was buffered with 21 grams of sodium acetate and 36 grams of zinc acetate. The mixture was stirred and heated to 160° C. to distill methanol. The temperature was increased to 240° C. during the distillation. After 1.5 hours, the mixture was transferred into a clave, which was connected to a vacuum pump. The clave pressure was reduced to 0.4 mm Hg while raising the temperature to 250° C. The reaction was stopped when the agitator reached 1250 watts. The copolyester obtained was discharged and quenched in water. The product was solid state polymerized at 200° C. for 4 hours to raise the intrinsic viscosity from 0.83 to 1.07 dl/g. The copolymer was spun into fibers.

Example VI
Comparison of inventive and conventional dyeability modifiers

This example showed that fibers made from poly (trimethylene terephthalate) containing the cationic dyeability modifier of the invention have improved dye exhaust performance over fibers made from polytrimethylene terephthalate) containing a conventional cationic dyeability modifier, namely, sodium sulfoisophthalate.

A portion of the fibers prepared in Comparative Example B (poly(trimethylene terephthalate)/sodium dimethyl sulfoisophthalate copolymer, designated polymer A in Table I), a portion of the fibers prepared in Example V (poly (trimethylene terephthalate)/sodium dimethyl-3-(2-sulfoethyl)adipate copolymer, designated polymer B in Table I), and a portion of the fibers prepared in Comparative Example A (polytrimethylene terephthalate) homopolymer, designated polymer C in Table I) were knitted into socks using a Fiber Analysis Knitter Model 121 (Lawson-Hemphill Company, Spartanburg, S.C.). The socks were dyed in aqueous dye bathes containing one weight percent of various Sevron dyes (Crompton & Knowles, Gibralter, Pa.) for one hour under varying conditions, as set forth in Table I. The dye absorptivity was measured using a Bausch & Lomb Spectronic 21 spectrophotometer (Spectronic Instruments, Inc., Rochester, N.Y.), using the wavelengths indicated in Table I. The dye concentrations were determined using a calibration curve, and the dye exhaust was calculated using the equation $\{(X-Y)/X\} \times 100\%$, where X is the initial concentration of dye in the dye bath, and Y is the concentration of dye after removal of the dyed fibers. The results are set forth in Table I, below:

TABLE I

| | | Sevron Dye Exhaust, % | | |
|---|---|---|---|---|
| Sample | Polymer | Blue (655 nm) | Red (510 nm) | Yellow (440 nm) |
| (no carrier, atmospheric pressure, 100° C.) | | | | |
| 1 | A | 55.8 | 2.3 | 23.7 |
| 2 | B | 38.0 | 21.0 | 26.1 |
| 3 | C | 0 | 0 | 0 |
| (with carrier,* atmospheric pressure, 100° C.) | | | | |
| 4 | A | 85.1 | 63.9 | 74.8 |
| 5 | B | 100.0 | 96.1 | 97.2 |
| (no carrier, 25.3 psi (1.746 × 10$^5$ N/m$^2$) pressure, 116° C.) | | | | |
| 6 | A | 75.3 | 60.9 | 65.1 |
| 7 | B | 98.6 | 97.4 | 96.7 |

*The carrier is Tanalon HIW ® (Sybron Chemicals, Inc.), a water emulsified, nonionic butyl benzoate carrier.

Example VII
Copolyamide containing dyeability modifier of the invention

A 35 pound autoclave was charged with 16,698 grams of 51.5% 6,6 salt solution (32.78 moles), 149.1 1 grams of 78.34% hexamethylene diamine solution (1.01 moles), and 231.54 grams (0.838 moles) of 3-(2-sulfoethyl)hexanedioic acid, sodium salt. The mixture was heated to 272° C. and 250 pounds per square inch (1.72×10$^6$N/m$^2$) pressure. Over a period of 30 minutes, the pressure was reduced to atmospheric. After one hour steam finish, the polymer was extruded and cut into flakes. As a control, nylon 6,6 homopolymer was prepared using the same procedure, but omitting the hexamethylene diamine solution and the 3-(2-sulfoethyl)hexanedioic acid, sodium salt. The flakes of the copolyamide and nylon 6,6 homopolymer were each spun into fiber yarn at 285° C. A portion of the copolyamide fibers and a portion of the nylon 6,6 homopolymer were each knitted into socks, and the socks were dyed in aqueous dye bathes containing one weight percent of various Sevron dyes for one hour at 100° C. under atmospheric pressure, using no carrier. The dye absorptivity was measured in the same manner as described in Example VI, and the results are shown in the following Table II.

TABLE II

| Polymer | Sevron Dye Exhaust, % | | |
|---|---|---|---|
| | Blue (655 nm) | Red (510 nm) | Yellow (440 nm) |
| Nylon 6,6 homopolymer | 10.7 | 10.8 | 8.8 |
| Copolyamide | 94.5 | 63.5 | 94.5 |

What is claimed is:

1. A cationic dyeability modifier for incorporation into polyesters and polyamides to increase their affinity for basic dyes, said cationic dyeability modifier having the following formula:

$$R_1OOC-(CH_2)_n-CH(CH_2CH_2SO_3X)-(CH_2)_m-COOR_2$$

where n is an integer from 1 to 10, m is an integer from 1 to 10, X is an alkali metal selected from the group consisting of lithium, sodium and potassium, and $R^1$ and $R_2$ are independently hydrogen or alkyl groups having one to four carbon atoms.

2. The cationic dyeability modifier according to claim 1, wherein said cationic dyeability modifier is selected from the group consisting of alkali metal salts of 3-(2-sulfoethyl) hexanedioic acid and alkali metal salts of dimethyl-3-(2-sulfoethyl)adipate.

3. The cationic dyeability modifier according to claim 1, wherein said cationic dyeability modifier is selected from the group consisting of sodium salts of 3-(2-sulfoethyl) hexanedioic acid, and dimethyl-3-(2-sulfoethyl)adipate.

4. A basic dyeable copolymer selected from the group consisting of copolyesters and copolyamides, wherein said copolymer comprises a comonomer of the formula:

$$R_1OOC-(CH_2)_n-CH(CH_2CH_2SO_3X)-(CH_2)_m-COOR_2$$

where n is an integer from 1 to 10, m is an integer from 1 to 10, X is an alkali metal selected from the group consisting of lithium, sodium and potassium, and $R_1$ and $R_2$ are independently hydrogen or alkyl groups having one to four carbon atoms, and wherein said comonomer is incorporated into the polymer chain of said copolymer in an amount sufficient to improve its affinity for basic dyes.

5. The copolymer according to claim 4, wherein said copolymer comprises from 0.5 to 4 mole percent of said comonomer.

6. The copolymer according to claim 4, wherein said copolymer comprises from 1 to 2 mole percent of said comonomer.

7. The copolymer according to claim 4, wherein said comonomer is selected from the group consisting of alkali metal salts of 3-(2-sulfoethyl)hexanedioic acid and alkali metal salts of dimethyl-3-(2-sulfoethyl)adipate.

8. The copolymer according to claim 4, wherein said comonomer is selected from the group consisting of sodium salts of 3-(2-sulfoethyl)hexanedioic acid, and dimethyl-3-(2-sulfoethyl)adipate.

9. The copolymer according to claim 4, wherein said copolymer is a copolyamide derived from a polyamide selected from the group consisting of nylon 6, nylon 66 and copolymers thereof.

10. The copolymer according to claim 4, wherein said copolymer is a copolyester derived from a poly(alkylene terephthalate) selected from the group consisting of poly (ethylene terephthalate), poly(trimethylene terephthalate), poly(butylene terephthalate), and copolymers thereof.

11. The copolymer according to claim 4, wherein said copolymer is a copolyester derived from poly(trimethylene terephthalate), and said comonomer is selected from the group consisting of sodium salts of 3-(2-sulfoethyl) hexanedioic acid, and dimethyl-3-(2-sulfoethyl)adipate.

12. The copolymer according to claim 4 in the form of a fiber.

13. A process for preparing a basic dyeable copolyester comprising the steps of:

(a) combining one or more materials selected from the group consisting of poly(alkylene terephthalate)-forming monomers and polyoxyalkylene glycol oligomers with a comonomer of the formula:

$$R^1OOC-(CH_2)_n-CH(CH_2CH_2SO_3X)-(CH_2)_m-COOR_2$$

where n is an integer from 1 to 10, m is an integer from 1 to 10, X is an alkali metal selected from the group consisting of lithium, sodium and potassium, and $R_1$ and $R_2$ are independently hydrogen or alkyl groups having one to four carbon atoms; and (b) mixing and heating said materials and said comonomer at a temperature sufficient to cause copolymerization to form a copolyester containing said comonomer in an amount sufficient to improve its affinity for basic dyes.

14. The process according to claim 13, wherein said copolyester contains from 0.5 to 4 mole percent of said comonomer.

15. The process according to claim 13, wherein said copolyester contains from 1 to 2 mole percent of said comonomer.

16. The process according to claim 13 further comprising the step of extruding said copolyester to form a fiber.

17. The process according to claim 13, wherein said comonomer is selected from the group consisting of alkali metal salts of 3-(2-sulfoethyl)hexanedioic acid and alkali metal salts of dimethyl-3-(2-sulfoethyl)adipate.

18. The process according to claim 13, wherein said comonomer is selected from the group consisting of sodium salts of 3-(2-sulfoethyl)hexanedioic acid, and dimethyl-3-(2-sulfoethyl)adipate.

19. The process according to claim 13, wherein said poly(alkylene terephthalate) is selected from the group consisting of poly(ethylene terephthalate), poly(trimethylene terephthalate), poly(butylene terephthalate), and copolymers thereof.

20. The process according to claim 13, wherein said poly(alkylene terephthalate) is poly(trimethylene terephthalate).

21. A dyed composition prepared by dyeing the composition of claim.

22. A dyed fiber prepared by dyeing the fiber of claim 12.

23. A dyed shaped article prepared from the composition of claim 4.

24. A dyeing process, comprising providing the composition of claim 4 and dyeing the composition.

* * * * *

UNITED STATES PATENT AND TRADEMARK OFFICE
CERTIFICATE OF CORRECTION

PATENT NO.    : 6,312,805 B1
DATED         : November 6, 2001
INVENTOR(S)   : Yanhui Sun It is certified that error appears in the above-identified patent and that said Letters Patent is hereby corrected as shown below:

<u>Column 9,</u>
Line 26, replace "$R^1$" with -- $R_1$ --

<u>Column 10,</u>
Line 21, replace "$R^1$" with -- $R_1$ --

Signed and Sealed this

Sixteenth Day of July, 2002

*Attest:*

JAMES E. ROGAN
*Attesting Officer*    *Director of the United States Patent and Trademark Office*